(12) United States Patent
Chang et al.

(10) Patent No.: US 8,158,358 B2
(45) Date of Patent: Apr. 17, 2012

(54) METHOD FOR GENDER IDENTIFICATION OF EAGLES WITH PROBE-BASED REAL-TIME PCR AND THE SEQUENCES USED FOR GENDER IDENTIFICATION OF EAGLES

(75) Inventors: Hsueh-Wei Chang, Kaohsiung (TW); Chien-Chung Cheng, Taipei (TW); De-Leung Gu, Sindian (TW); San-Hua Su, Pingtung (TW)

(73) Assignee: Kaohsiung Medical University, Kaohsiung (TW)

( * ) Notice: Subject to any disclaimer, the term of this patent is extended or adjusted under 35 U.S.C. 154(b) by 604 days.

(21) Appl. No.: 12/209,193

(22) Filed: Sep. 11, 2008

(65) Prior Publication Data

US 2009/0081677 A1 Mar. 26, 2009

(30) Foreign Application Priority Data

Sep. 26, 2007 (TW) .............................. 96135735 A

(51) Int. Cl.
*C12Q 1/68* (2006.01)
*C12P 19/34* (2006.01)

(52) U.S. Cl. ...................... 435/6.12; 435/6.1; 435/6.11

(58) Field of Classification Search ........................ None
See application file for complete search history.

(56) References Cited

OTHER PUBLICATIONS

Chang et al., "High-throughput gender identification of Accipitridae eagles with real-time PCR using TaqMan probes," Theriogenology, Jun. 2008, vol. 70, pp. 83-90.*
Virta et al., "Sex determination of bovine embryo blastomeres by fluorogenic probes," Theriogenology, 2002, vol. 57, pp. 2229-2236.*
Chang et al., "An improved PCR method for gender identification of eagles", Molecular and Cellular Probe, 2008, Elsevier Ltd.
Chang et al., "High-throughput gender identification of Accipitridae eagles with real-time PCR using TaqMan probes", ScienceDirect, Theriogenology, 2008, Elsevier Inc.
Chang et al., "High-throughput avian molecular sexing by SYBR green-bases real-time PCR combined with melting curve analysis", BMC Biotechnology 2008, 8:12, Feb. 12, 2008.

* cited by examiner

*Primary Examiner* — Young J Kim
(74) *Attorney, Agent, or Firm* — Pai Patent & Trademark Law Firm; Chao-Chang David Pai

(57) ABSTRACT

A method for gender identification of eagles includes: providing a DNA of an eagle; performing a probe-based real-time PCR using the DNA as a template, a universal primer pair P2/P8 as a primer pair and a first probe and a second probe as probes, wherein the 5' ends of the first probe and the second probe are labeled with a first fluorescent dye and a second fluorescent dye, respectively, and the first probe is a sequence with about 15-38 nucleotides in length of SEQ ID No. 1 and the second probe is a sequence with about 15-44 nucleotides in length of SEQ ID No. 2; and analyzing a result of the PCR, wherein if the result is positive for both the first and the second fluorescent dye, the eagle is a female, and if the result is positive for only the first fluorescent dye, the eagle is a male.

12 Claims, 10 Drawing Sheets

```
                        SEQUENCE LISTING

<160> NUMBER OF SEQ ID NOS: 28

<210> SEQ ID NO 1
<211> LENGTH: 38
<212> TYPE: DNA
<213> ORGANISM: Artificial Sequence
<220> FEATURE:
<223> OTHER INFORMATION: Eagle Gender Probe

<400> SEQUENCE: 1
tcccttcact tccattaaag ctgatctgga atttcaga                              38

<210> SEQ ID NO 2
<211> LENGTH: 44
<212> TYPE: DNA
<213> ORGANISM: Artificial Sequence
<220> FEATURE:
<223> OTHER INFORMATION: Eagle Gender Probe

<400> SEQUENCE: 2
gtgtgccayg tgtgaaaacc acccaaccca aaagtacaag acaa                       44

<210> SEQ ID NO 3
<211> LENGTH: 28
<212> TYPE: DNA
<213> ORGANISM: Artificial Sequence
<220> FEATURE:
<223> OTHER INFORMATION: Eagle Gender Probe

<400> SEQUENCE: 3
cccttcactt ccattaaagc tgatctgg                                        28

<210> SEQ ID NO 4
<211> LENGTH: 24
<212> TYPE: DNA
<213> ORGANISM: Artificial Sequence
<220> FEATURE:
<223> OTHER INFORMATION: Eagle Gender Probe

<400> SEQUENCE: 4
tgtgccatgt gtgaaaacca ccca                                            24

<210> SEQ ID NO 5
<211> LENGTH: 20
<212> TYPE: DNA
<213> ORGANISM: Artificial Sequence
<220> FEATURE:
<223> OTHER INFORMATION: P2 primer

<400> SEQUENCE: 5
tctgcatcgc taaatccttt                                                 20

<210> SEQ ID NO 6
<211> LENGTH: 20
```

```
<212> TYPE: DNA
<213> ORGANISM: Artificial Sequence
<220> FEATURE:
<223> OTHER INFORMATION: P8 primer

<400> SEQUENCE: 6
ctcccaagga tgagraaytg                                                    20

<210> SEQ ID NO 7
<211> LENGTH: 24
<212> TYPE: DNA
<213> ORGANISM: Artificial Sequence
<220> FEATURE:
<223> OTHER INFORMATION: Eagle Gender Probe

<400> SEQUENCE: 7
tgggtggttt tcacacgtgg caca                                               24

<210> SEQ ID NO 8
<211> LENGTH: 328
<212> TYPE: DNA
<213> ORGANISM: Spilornis cheela hoya

<400> SEQUENCE: 8
tctcccaagg atgaggaatt gtgcaaaaca ggtgtctttt ggttttgact gacttgtgct        60
tttatattgc tattggttta gtttctttgt tgggggtgt tgttgggttt tggttttttaa      120 gttggttttt tttttccttt tctgaacaca tattttgac aggctaggta aaactttact       180
tatggttgtt aatcacatag ctttgaacta cctattctga aattccagat cagctttaat      240
ggaagtgaag ggagacgcag taggagcaga agatactctg gatctgatag tgactccatc      300
tcagaaagaa aacggcctaa aaaacgtg                                          328

<210> SEQ ID NO 9
<211> LENGTH: 341
<212> TYPE: DNA
<213> ORGANISM: Spilornis cheela hoya

<400> SEQUENCE: 9
tctcccaagg atgaggaatt gtgcaaaaca ggtatctctg gttttgacc aactaacttt        60 gatttttttg ttgttgtttt tgtttgtttt tttcattgct gttgtcttgt cttgtacttt     120
tgggttgggt ggttttcaca catggcacac ccccccattc ccccattttt gacaggctag     180
ataacacatt aataaaatgt tttagtcacg tagctttgaa ctacttaatc tgaaattcca     240
gatcagcttt aatggaagtg aagggaaacg cagtaggagc agaagatatt ctggatctga     300
tagtgactcc atctcggaaa gaaaacgacc aaaaaaacgt g                          341

<210> SEQ ID NO 10
<211> LENGTH: 378
<212> TYPE: DNA
<213> ORGANISM: Circaetus gallicus

<400> SEQUENCE: 10
ctcccaagga tgaggaactg tgcaaaacag gtgtctcttg gttctgactg acttgtactt        60
ttatattgct attggtttag tttctttgtt ggggttgtt gttgggtttt ggttttaag       120 ttggtttttt tttcctttc tgaacacata ttttgacag gctaggtaaa actttattta       180
tggttgttaa tcacgtagct ttgaactacc tattctgaaa ttccagatca gctttaatgg      240
aagtgaaggg agacgcagta ggagcagaag atactctgga tctgatagtg actccatctc      300
agaaagaaaa cggcctaaaa aacgtggaag accacgaact attcctcgag aaaatattaa      360
```
aggatttagc gatgcaga    378

<210> SEQ ID NO 11
<211> LENGTH: 387
<212> TYPE: DNA
<213> ORGANISM: Circaetus gallicus

<400> SEQUENCE: 11
ctcccaagga tgagaaactg tgcaaaacag gtatctctgg gttttgacca actaactttg    60
atttttttg ttgtttgttt gttttttcat tgctgttgtt ttgtcttgta cttttgggct    120
gggtggtttt cacacatggc acacccccc attcccccat ttttgacagg ctagataaca    180
cattaataaa atgttttagt cacgtagctt tgaactactt aatctgaaat tccagatcag    240
ctttaatgga agtgaaggga aacgcagtag gagcagaaga tattctggat ctgatagtga    300
ctccatctca gaaagaaaac gaccaaaaaa acgtggacga ccacgaacta ttcctcgaga    360
aaatattaaa ggatttagcg atgcaga    387

<210> SEQ ID NO 12
<211> LENGTH: 370
<212> TYPE: DNA
<213> ORGANISM: Gyps indicus

<400> SEQUENCE: 12
tttctccccc aggggaggga aattggcaaa acaggggttt tttggttttg acggacttga    60
acttttaaat tgcaattggt ttagtttttt tttggggggg gttggggttt tggttttttaa    120
atgggttttt tttttttttt ttttttccttt tctgaacaca tattttttgac aggctaggta    180
aaactttatt tacggttgtt aatcacgtag ctttgaacta cctattctga aattccagat    240
cagctttaat ggaagtgaag ggagacgcag taggagcaga agatactctg gatccgatag    300
tgactccatc tcagaaagaa aacggcctaa aaaacgtgga agaccacgaa ctagtcctcg    360
agaaaatatt    370

<210> SEQ ID NO 13
<211> LENGTH: 372
<212> TYPE: DNA
<213> ORGANISM: Gyps indicus

<400> SEQUENCE: 13
ctcccaagga tgaagaaact gtgcaaaaca ggtatcttct aggttttaca actaaatttg    60
atttttttat tgttgtggtt tgtttgtttt ttcattactg ttgttttgtc ttgtacttttt    120
gggttgggtg gttttcacac atggcacacc ccccattcc cccattttg acaggctaga    180
taacatatta ataaaatgtt ttagtcacgt agctttgaac tacttaatct gaaattccag    240
atcagcttta atggaagtga agggaaacgc agtaggagca gaagatattg ctggatctga    300
tagtgactcc atctcagaaa gaaaacgacc aaaaaaacgt ggacgaccac gaatactcgt    360
cgagaaaata tt    372

<210> SEQ ID NO 14
<211> LENGTH: 370
<212> TYPE: DNA
<213> ORGANISM: Gyps bengalensis

<400> SEQUENCE: 14
tttcctcccc aaggggggga aatgtgcaaa aagggggttt cttggttctg accgacctgg    60
aactttaata ttggcattgg gttagttttt tttttggggg ggggtggggt ttgggttttta    120

```
aagtgggttt ttttttttt ttttttcctt ttctgaacac atattttga caggctaggt      180 aaaactttat ttacggttgt taatcacgta gctttgaact acctattctg aaattccaga    240
tcagctttaa tggaagtgaa gggagacgca gtaggagcag aagatactct ggatccgata   300
gtgactccat ctcagaaaga aacggccta aaaaacgtga agaccacgaa ctattcctcg    360
agaaaatatt                                                          370

<210> SEQ ID NO 15
<211> LENGTH: 371
<212> TYPE: DNA
<213> ORGANISM: Gyps bengalensis

<400> SEQUENCE: 15
ctcccaagga tgaggaaact gtgcaaaaca ggtatcttct gggttttgac caactaaatt    60
tgattttttt gttgttgttt gtttgttttt tcattgctgt tgttttgtct tgtacttttg   120
ggttgggtgg ttttcacaca tggcacaccc ccccattccc ccattttga caggctagat   180 aacatattaa taaatgtttt tagtcacgta gctttgaact acttaatctg aaattccaga   240
tcagctttaa tggaagtgaa gggaaacgca gtaggagcag aagatattgc tggatctgat   300
agtgactcca tctcagaaag aaaacgacca aaaaaacgtg gacgaccacg aatactcgtc   360
gagaaaatat t                                                        371

<210> SEQ ID NO 16
<211> LENGTH: 343
<212> TYPE: DNA
<213> ORGANISM: Accipiter nisus

<400> SEQUENCE: 16
tgcaaaacag gtatctctgg gttttgaaca actaactgat ttttttgttg ttgtttgttt    60
tttcattgct gttgttttgt cttgtacttt tgggttgggt ggttttcaca cgtggcacac   120
ccccccattc ccccatttt gacaggctag ataacacatt aataaaatgt tttagtcaca   180
tagctttaaa ctacttaatc tgaaattcca gatcagcttt aatggaagtg aagggaaacg   240
cagtaggagc agaagatatt ctggatctga tagtgactcc atctcagaaa gaaaacgacc   300
aaaaaaacgt ggacgaccac gaactattcc tcgagaaaat att                      343

<210> SEQ ID NO 17
<211> LENGTH: 347
<212> TYPE: DNA
<213> ORGANISM: Accipiter nisus

<400> SEQUENCE: 17
tgcaaaacag gtgtctcttg gttttgactg acttgtactt tttatattac tattggttta    60
gtttctttgt tgggggttgt tgttgtgttt tggttcttaa gttgtttgtt ttttttttt    120 ctccttttct gaacacatat ttttgacagg ctaggtaaaa ctttgtttat ggttgttaat   180
cacgtagctt tgaactacct attctgaaat tccagatcag ctttaatgga agtgaaggga   240
gacgcagtag gagcagaaga tactctggat cagatagtga ctccgtctca gaaagaaaac   300
ggcctaaaaa acgtggaaga ccacgaacta ttcctcgaga aaatatt                  347

<210> SEQ ID NO 18
<211> LENGTH: 351
<212> TYPE: DNA
<213> ORGANISM: Spizaetus nipalensis

<400> SEQUENCE: 18
```

```
tgcaaaacag gtatctctgg gttttgacca actaactgat ttttttgttg ttgtttgttt      60 gtttttcat tgctgttgtt ttgtcttgta cttttgggtt gggtggtttt cacacgtggc      120
acaccccccc ccccgttccc ccattttga caggctagat aacacattaa taaaatgttt      180
tagtcacgta ggtttgaact acttaatctg aaattccaga tcagctttaa tggaagtgaa     240
gggaaacgca gtaggagcag aagatattct ggatctgata gtgactccat ctcagaaaga    300
aaacgaccaa aaaaacgtgg acgaccacga actattcctc gagaaaatat t             351
```

<210> SEQ ID NO 19
<211> LENGTH: 343
<212> TYPE: DNA
<213> ORGANISM: Spizaetus nipalensis

<400> SEQUENCE: 19

```
tgcaaaacag gtgtctcttg gttctgactg acttgtactt ttatatcgct attggtttag     60
tttctttgtg gggggttgtt gttgagtttt ggttttaag ttgtggggtt ttttttttc      120 ttttctgaac acatattttt gacaggctag gtaaagcttt atttatggtt gttaatcacg    180
tagctttcaa ctacctattc tgaaattcca gatcagcttt aatggaagtg aagggagacg   240
cagtaggagc agaagatact ctggatctga tagtgactcc atctcagaaa gaaaacggcc   300
taaaaaacgt ggaagaccac gaactattcc tcgagaaaat att                     343
```

<210> SEQ ID NO 20
<211> LENGTH: 347
<212> TYPE: DNA
<213> ORGANISM: Aquila chrysaetos

<400> SEQUENCE: 20

```
tgcaaaacag gtatctctgg gttttgacca actaactgat ttttttgttg ttgtttgttt     60 gtttttcat tgctgttgtt ttgtcttgta cttttgggtt gggtggtttt cacacgtggc    120
acactccccc gttccccat ttttgacagg ctagataaca cattaataaa atgttttagt    180
cacgtaggtt tgaactactt aatctgaaat tccagatcag ctttaatgga agtgaaggga    240
aacgcagtag gagcagaaga tattctggat ctgatagtga ctccatctca gaagaaaac    300 gaccaaaaaa acgtggacga ccacgaacta ttcctcgaga aaatatt                 347
```

<210> SEQ ID NO 21
<211> LENGTH: 344
<212> TYPE: DNA
<213> ORGANISM: Aquila chrysaetos

<400> SEQUENCE: 21

```
tgcaaaacag gtgtctcttg gttctgactg acttgtactt ttatattgct attggtttag    60
tttctttgtt gggggttatt gttgggtttt ggttttaag ttgtgttttg ttttttttt    120 cttttctgaa cacatattttt tgacaggcta ggtaaagctt tatttatggt tgttaatcgc   180
gtagctttga actacctatt ctgaaattcc agatcagctt taatggaagt gaagggagac   240
gcagtaggag cagaagatac tctggatccg atagtgactc catctcagaa agaaaacggc  300
ctaaaaaacg tggaagacca cgaactattc ctcgagaaaa tatt                    344
```

<210> SEQ ID NO 22
<211> LENGTH: 343
<212> TYPE: DNA
<213> ORGANISM: Circus spilonotus

<400> SEQUENCE: 22

```
tgcaaaacag gtatctctgg gttttgaaca actaactgat ttttttgttg ttgtttgttt      60
tttcattgct gttgttttgt cttgtacttt tgggttgggt ggttttcaca cgtggcacac     120
ccccccattc cccatttttt gacaggctag ataacacatt aataaaatgt tttagtcaca     180 tagcttttaaa ctacttaatc tgaaattcca gatcagcttt aatggaagtg aagggaaatg    240
cagtaggagc agaagatatt ctggatctga tagtgactcc atctcagaaa gaaaacgacc     300
aaaaaaacgt ggacgaccac gaactattcc tcgagaaaat att                      343

<210> SEQ ID NO 23
<211> LENGTH: 347
<212> TYPE: DNA
<213> ORGANISM: Circus spilonotus

<400> SEQUENCE: 23
tgcaaaacag gtgtctcttg gttctgactg acttgtactt tttatattgc tattggttta     60
gtttctttgt tggggttgt tgttgtgttt tggttcttaa gttgttttgt ttttttttt     120 ctccttttct gaacacatat ttttaacagg ctaggtaaaa ctttgtttat ggttgttaat     180
cacgtagctt tgaactacct attctgaaat tccagatcag ctttaatgga agtgaaggga    240
gacgcagtag gagcagaaga tactctggat cagatagtga ctccatctca gaaagaaaac    300
ggcctaaaaa acgtggaaga ccacgaacta ttcctcgaga aaatatt                 347

<210> SEQ ID NO 24
<211> LENGTH: 344
<212> TYPE: DNA
<213> ORGANISM: Milvus migrans

<400> SEQUENCE: 24
tgcaaaacag gtatctctgg ttttgacca actaactgat tttttttgtt gttgtttgtt      60
ttttcattgc tgttgttttg tcttgtactt tgggttggg tggttttcac acgtggcaca    120 ccccccatt ccccatttt tgacaggcta gataacacat taataaaatg ttttagtcac     180
gtagctttga actacttaat ctgaaattcc agatcagctt taatggaagt gaagggaaac    240
gcagtaggag cagaagatat tctggatctg atagtgactc catctcagaa agaaaacgac    300 caaaaaacg tggacgacca cgaactattc ctcgagaaaa tatt                     344

<210> SEQ ID NO 25
<211> LENGTH: 342
<212> TYPE: DNA
<213> ORGANISM: Milvus migrans

<400> SEQUENCE: 25
tgcaaaacag gtgcctcttg gttctgactg acttgtactt ctatattgct attggtttag     60
tttctttgtt ggaggtggtt gttgttgggt ttcgttttt aagttggggg ttttttttcct   120 tttctgaata catattttttg acaggctagg taaaacttta tttacggttg ttaatcacgt    180
agctttgaac tacctattct gaaattccag atcagctta atggaagtga agggagacgc    240
agtaggagca agatactc tggatcagat agtgactcca tctcagaaag aaaacggcct     300
aaaaaacgtg gaagaccacg aactattcct cgagaaaata tt                     342

<210> SEQ ID NO 26
<211> LENGTH: 20
<212> TYPE: DNA
<213> ORGANISM: Artificial Sequence
<220> FEATURE:
<223> OTHER INFORMATION: P2 primer antisense
```

-continued

```
<400> SEQUENCE: 26
aaaggattta gcgatgcaga                                                       20

<210> SEQ ID NO 27
<211> LENGTH: 29
<212> TYPE: DNA
<213> ORGANISM: Artificial Sequence
<220> FEATURE:
<223> OTHER INFORMATION: Eagle Gender Probe

<400> SEQUENCE: 27
tgggytgggt ggttttcaca catggcaca                                             29

<210> SEQ ID NO 28
<211> LENGTH: 28
<212> TYPE: DNA
<213> ORGANISM: Artificial Sequence
<220> FEATURE:
<223> OTHER INFORMATION: Eagle Gender Probe

<400> SEQUENCE: 28
ccagatcagc tttaatggaa gtgaaggg                                              28
```

METHOD FOR GENDER IDENTIFICATION OF EAGLES WITH PROBE-BASED REAL-TIME PCR AND THE SEQUENCES USED FOR GENDER IDENTIFICATION OF EAGLES

CROSS REFERENCE TO RELATED APPLICATIONS

This Application claims priority of Taiwan Patent Application No. 96135735, filed on Sep. 26, 2007, the entirety of which is incorporated by reference herein.

BACKGROUND OF THE INVENTION

1. Field of the Invention

The present invention relates to gender identification of eagles, and in particular relates to gender identification of eagles with probe-based real-time PCR.

2. Description of the Related Art

Monitoring the population sex ratio of eagles is essential to prevent extinction. However, efforts to measure population sex ratios for sexually monomorphic birds, including eagles (Ararajuba 2003;11:65-73), often yield male-biased sex ratios (Proc Biol Sci 2004;271(Suppl 5):S321-3-4, Omis Scand 1987;18:122-8, and Curr Ornithol 1989;6:1-50). Many techniques exist for gender identification of monomorphic birds (Yi Chuan 2005;27:297-301). For instance, the Griffiths procedure, which uses the universal P2/ P8 primers (Mol Ecol 1998;7:1071-5), is a common tool for avian gender identification.

The Griffiths procedure is based on the intron length difference between the chromo-helicase-DNA-binding (CHD)-Z and CHD-W gene amplicons. In general, the gender of birds is identified by the P2/ P8-primed PCR, followed by electrophoresis. The CHD-W gene is unique to females, whereas the CHD-Z gene is found in both sexes (i.e., female, ZW, and male, ZZ). Samples with one band are regarded as males, whereas those with two bands are regarded as females. However, intron lengths between the CHD-Z and CHD-W genes usually vary among species (Mol Ecol 1998;7:1071-5, Auk 1998;115:1074-8, and J Avian Biol 1999;30:116-21.). Additionally, due to the limited length difference of the intron for CHD-Z and CHD-W genes, there is accumulating evidence (J Avian Biol 1999;30:116-21, Mol Cell Probes 2004; 18:193-6, J Raptor Res 2005;39:286-95, IBIS 2006;148:167-8 and Curr Sci 2007;92:659-62) that the gender of some avian species cannot be accurately determined by the PCR-based protocol alone. Specifically, the length difference in some eagles is extremely short (approximately 3 to 9-bp). Thus, several solutions have been proposed, such as using re-designed primers of the PCR (J Avian Biol 1999;30: 116-21 and BMC Biotechnol 2008;8:12.,13), PCR-restriction fragment of length polymorphism (RFLP) (Mol Cell Probes 2004;18:193-6 and Curr Sci 2007;92:659-62) and random amplified polymorphic DNA (RAPD) fingerprinting (Theriogenology 2007;67:328-33 and Theriogenology 2006; 65:1759-68). However, the methods are unable to provide universal primers for high-throughput gender identification for multiple species of eagles.

BRIEF SUMMARY OF THE INVENTION

The invention provides a method for gender identification of eagles with probe-based real-time PCR, comprising: (a) providing a DNA of an eagle; (b) performing a probe-based real-time PCR using the DNA as a template, a universal primer pair P2 and P8 as a primer pair and a first probe and a second probe as probes, wherein the 5' ends of the first probe and the second probe are labeled with a first fluorescent dye and a second fluorescent dye, respectively, the 3' ends of the first probe and the second probe are both labeled with quencher dyes and the first fluorescent dye is different from the second fluorescent dye, and wherein a sequence of the first probe is a sequence with about 15-38 nucleotides in length of SEQ ID No. 1 or the complementary sequence thereof and a sequence of the second probe is a sequence with about 15-44 nucleotides in length of SEQ ID No. 2 or the complementary sequence thereof; and (c) analyzing a result of the probe-based real-time PCR, wherein if the result is positive for both the first and the second fluorescent dye, the eagle is a female, and if the result is positive for only the first fluorescent dye, the eagle is a male.

The invention further provides a nucleotide sequence used for gender identification of eagles comprising SEQ ID. No. 3 or the complementary sequence thereof.

The invention also provides a nucleotide sequence used for gender identification of eagles, comprising SEQ ID. No. 4 or the complementary sequence thereof.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

Figure 2B:
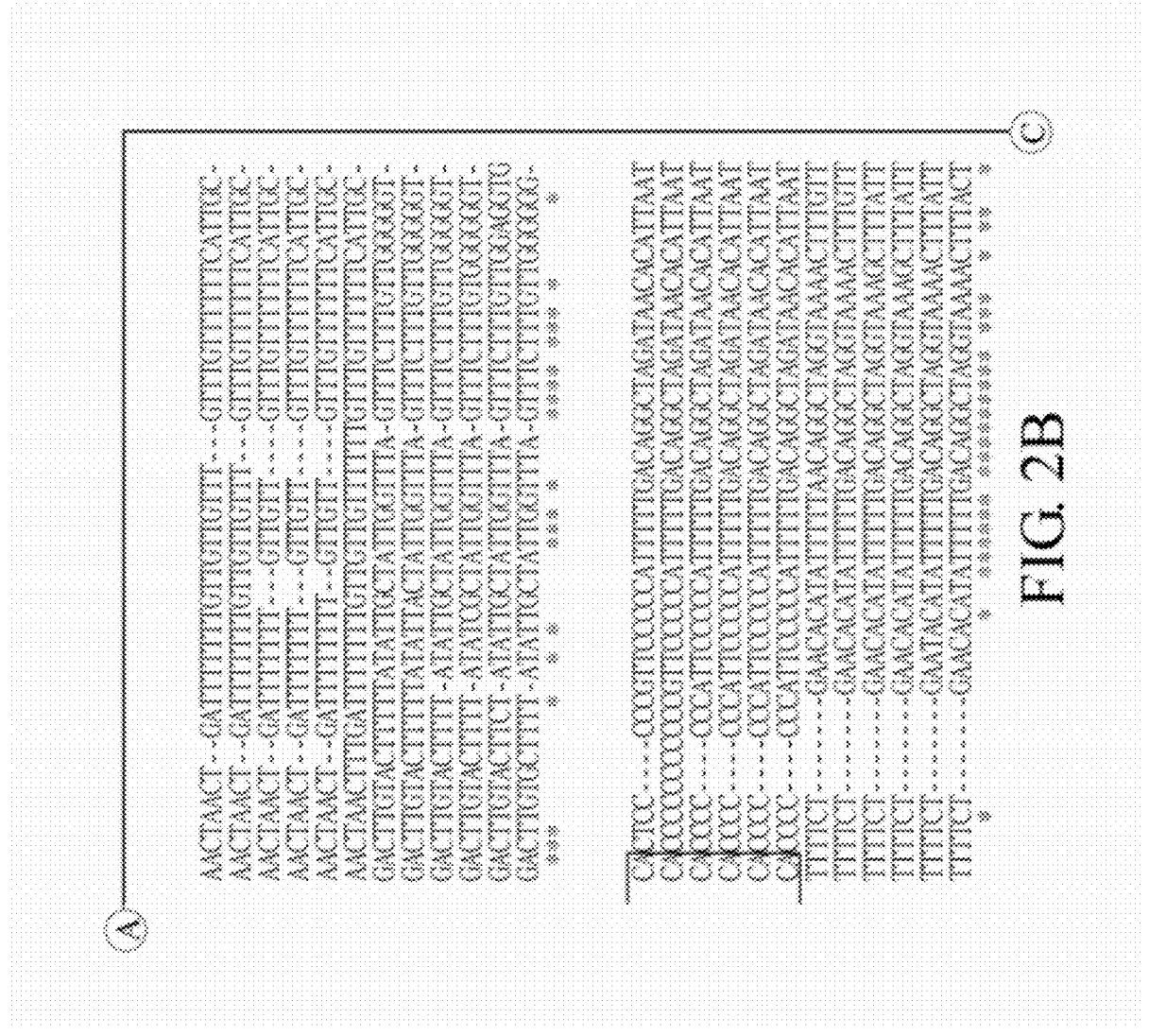
Figure 2C:
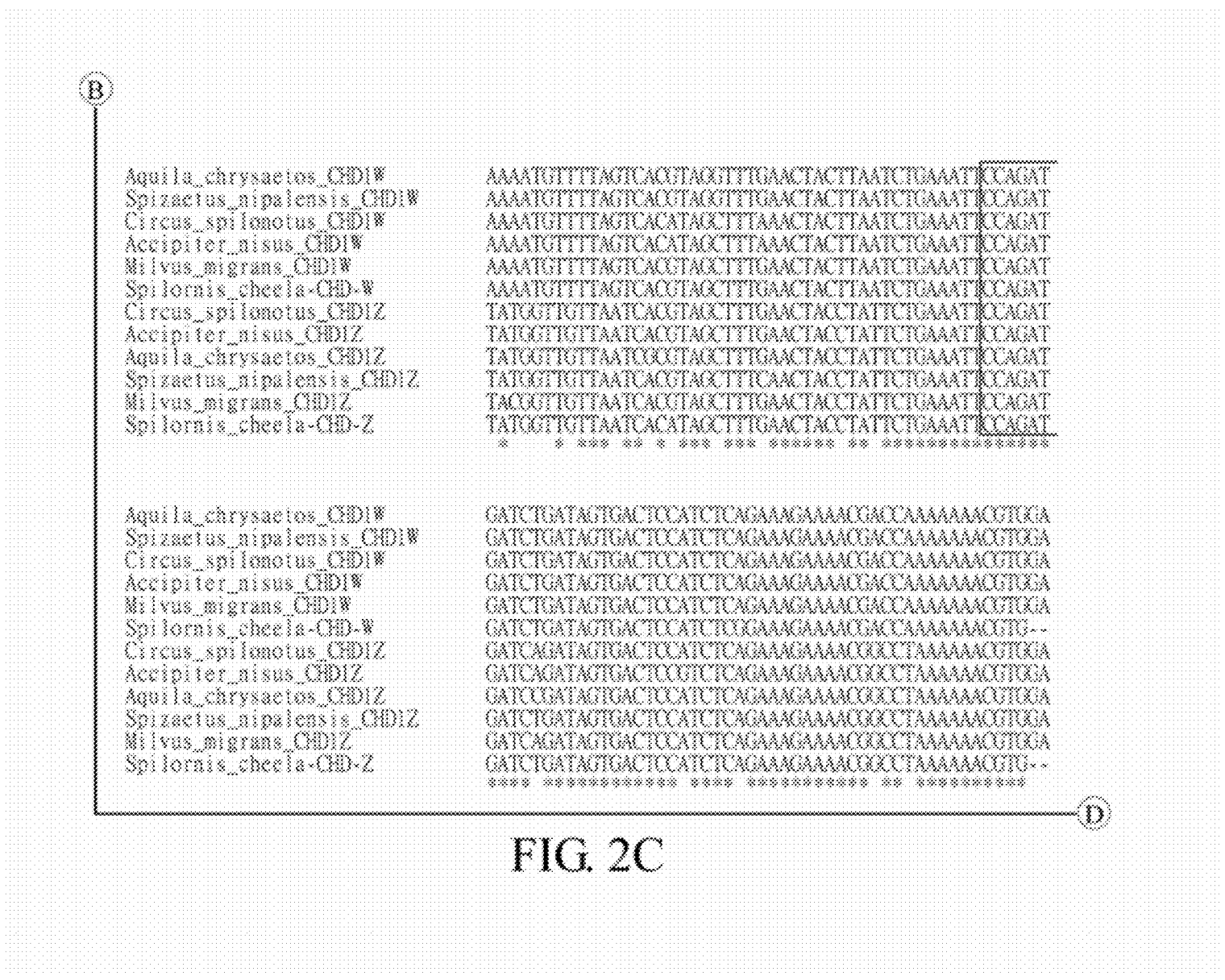

FIGS. 2A-2D shows sequence alignment of the CHD-Z and CHD-W genes amplified by P2/P8 primers in *Accipiter nisus, Spizaetus nipalensis, Aquila chrysaetos, Circus spilonotus* and *Milvus migrans*. The sequence for *Aquila chrysaetos* CHD1W is indicated by SEQ ID NO:20, the sequence for *Spizaetus nipalensis* CHD1W is indicated by SEQ ID NO:18, the sequence for *Circus spilonotus* CHD1W is indicated by SEQ ID NO:22, the sequence for *Accipiter nisus* CHD1W is indicated by SEQ ID NO:16, the sequence for *Milvus migrans* CHD1W is indicated by SEQ ID NO:24 and the sequence for *Spilornis cheela*-CHD-W is indicated by SEQ ID NO:9. Moreover, *Circus spilonotus* CHD1Z is indicated by SEQ ID NO:23, the sequence for the sequence for *Accipiter nisus* CHD1Z is indicated by SEQ ID NO:17, the sequence for *Aquila chrvsaetos* CHD1Z is indicated by SEQ ID NO:21, the sequence for *Spizaetus nipalensis* CHD1Z is indicated by SEQ ID NO:19, the sequence for *Milvus migrans* CHD1Z is indicated by SEQ ID NO:25 and the sequence for

*Spilornis cheela*-CHD-Z is indicated by SEQ ID NO:8. P8 primer is indicated by SEQ ID NO:6 and P2 primer (antisense) is indicated by SEQ ID NO:26. CHD-W-specific probe is indicated by SEQ ID NO:7 and CHD-ZW-common probe is indicated by SEQ ID NO:28.

Figure 1A:
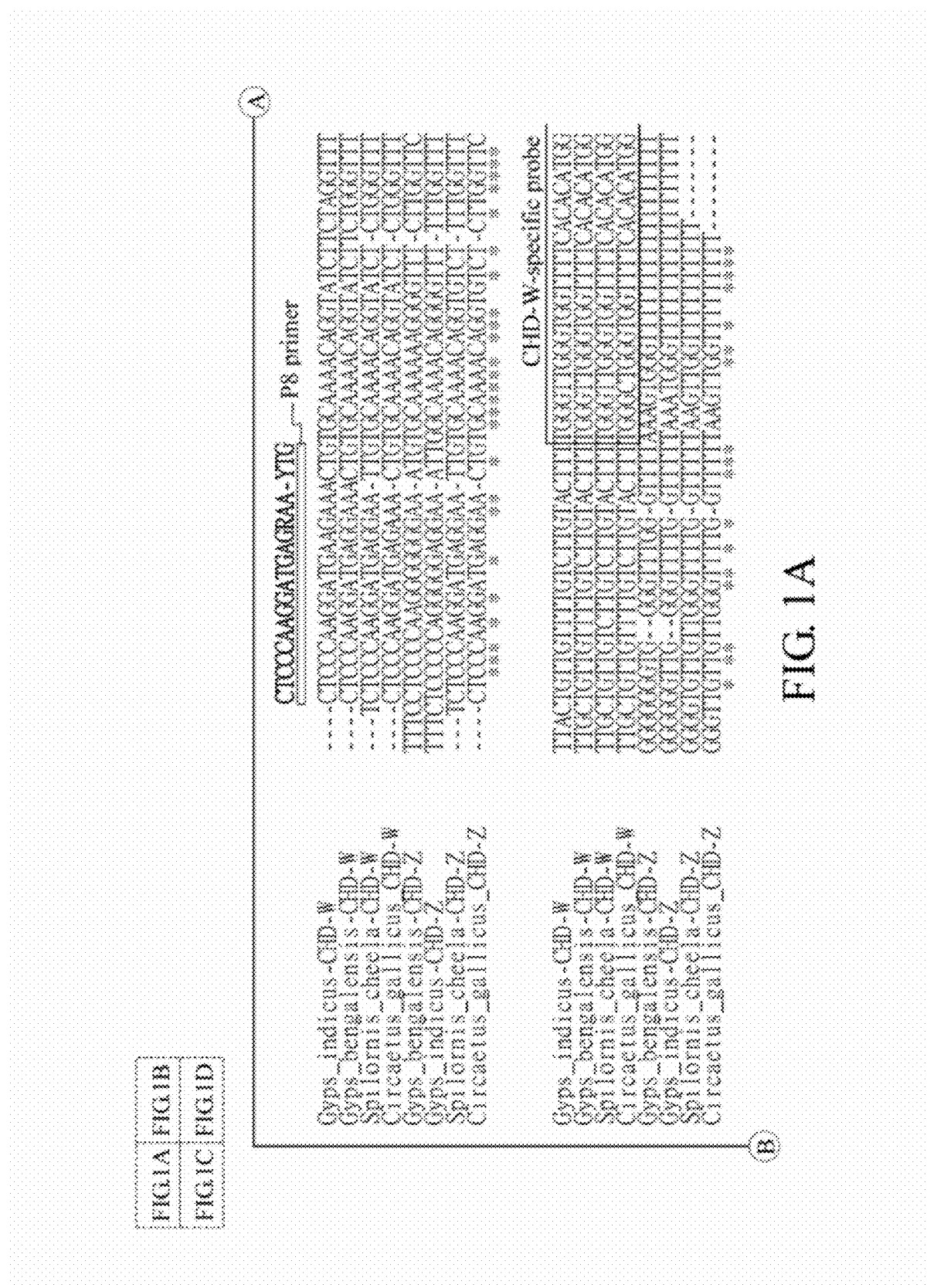
FIGS. 1A-1D shows sequence alignment of the CHD-Z and CHD-W genes amplified by P2/P8 primers in *Circaetus gallicus, Gyps indicus, Gyps bengalensis* and *Spilornis cheela hoya*. The sequence for *Gvps indicus*-CHD-W is indicated by SEQ ID NO:13, the sequence for *Gyps bengalensis*-CHD-W is indicated by SEQ ID NO:15, the sequence for *Spilornis cheela*-CHD-W is indicated by SEQ ID NO:9 and the sequence for *Circaetus gallicus* CHD-W is indicated by SEQ ID NO:11. Moreover, the sequence for *Gyps bengalensis*-CHD-Z is indicated by SEQ ID NO:14, the sequence for *Gyps indicus*-CHD-Z is indicated by SEQ ID NO:12, the sequence for *Spilornis cheela*-CHD-Z is indicated by SEQ ID NO:8 and the sequence for *Circaetus gallicus* CHD-Z is indicated by SEQ ID NO:10. P8 primer is indicated by SEQ ID NO:6 and P2 primer (antisense) is indicated by SEQ ID NO:26. CHD-W-Specific probe is indicated by SEQ ID NO:27 and CHD-ZW-common probe is indicated by SEQ ID NO:28.
Figure 1B:
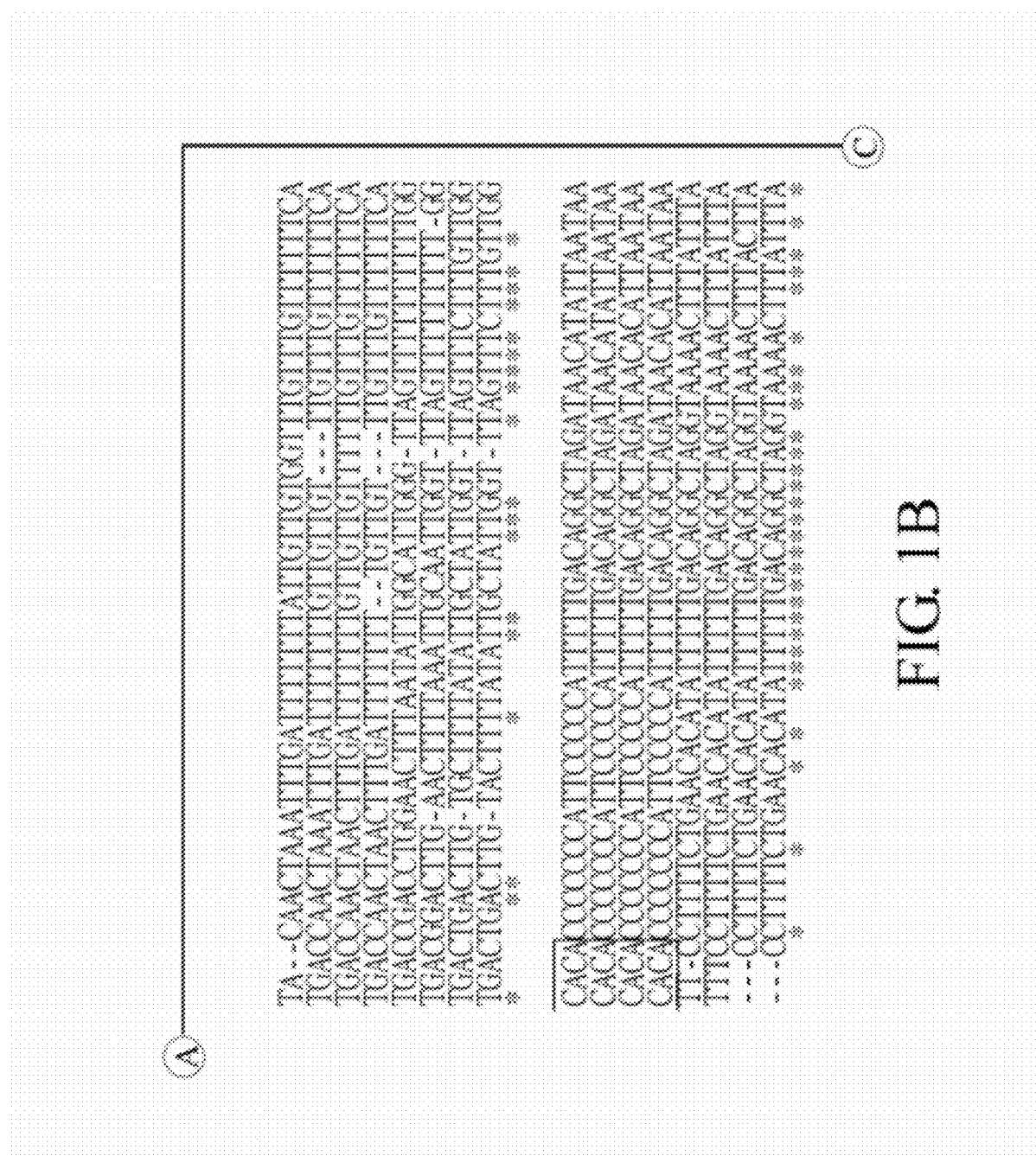
Figure 1C:
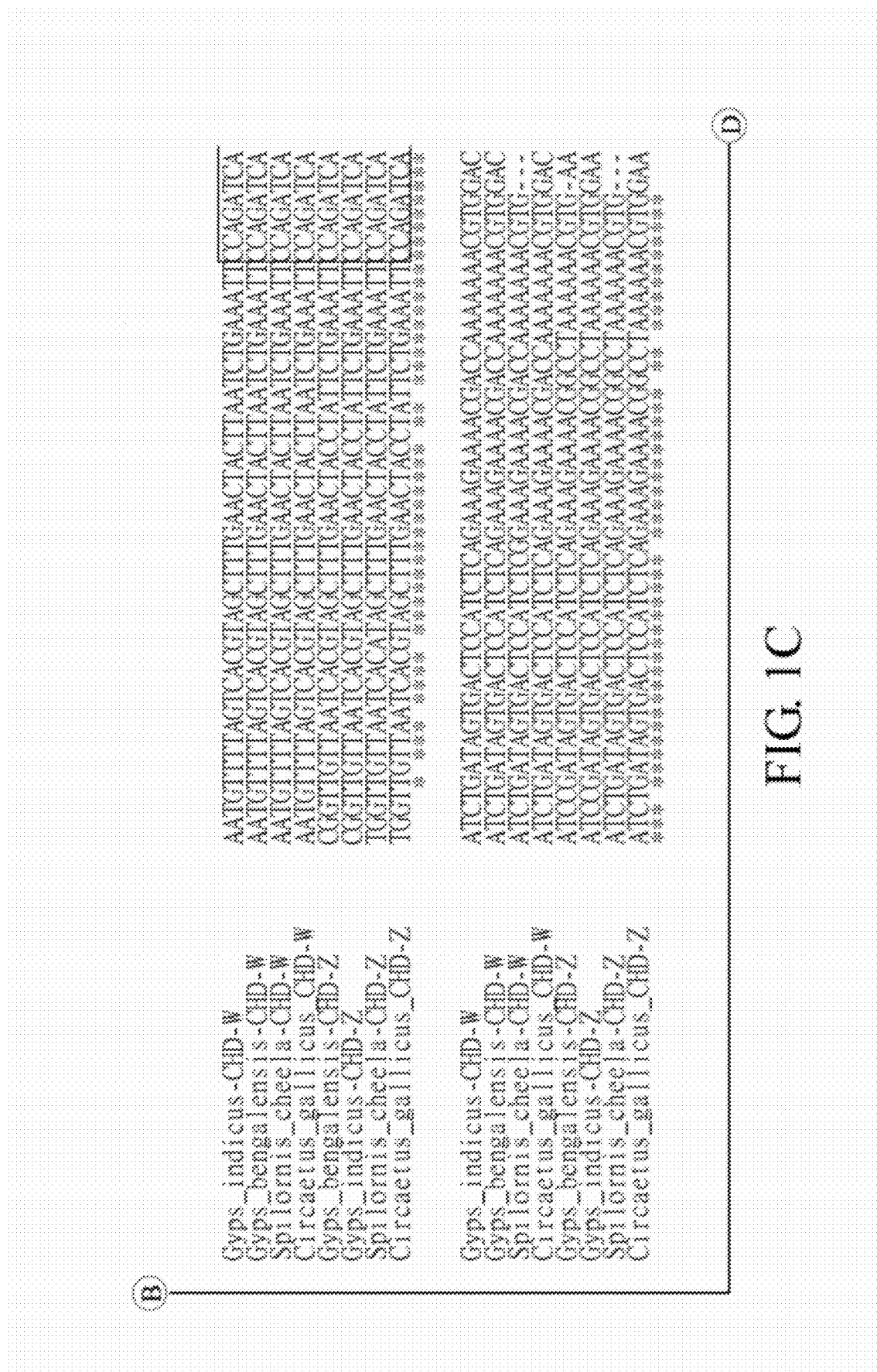
Figure 1D:
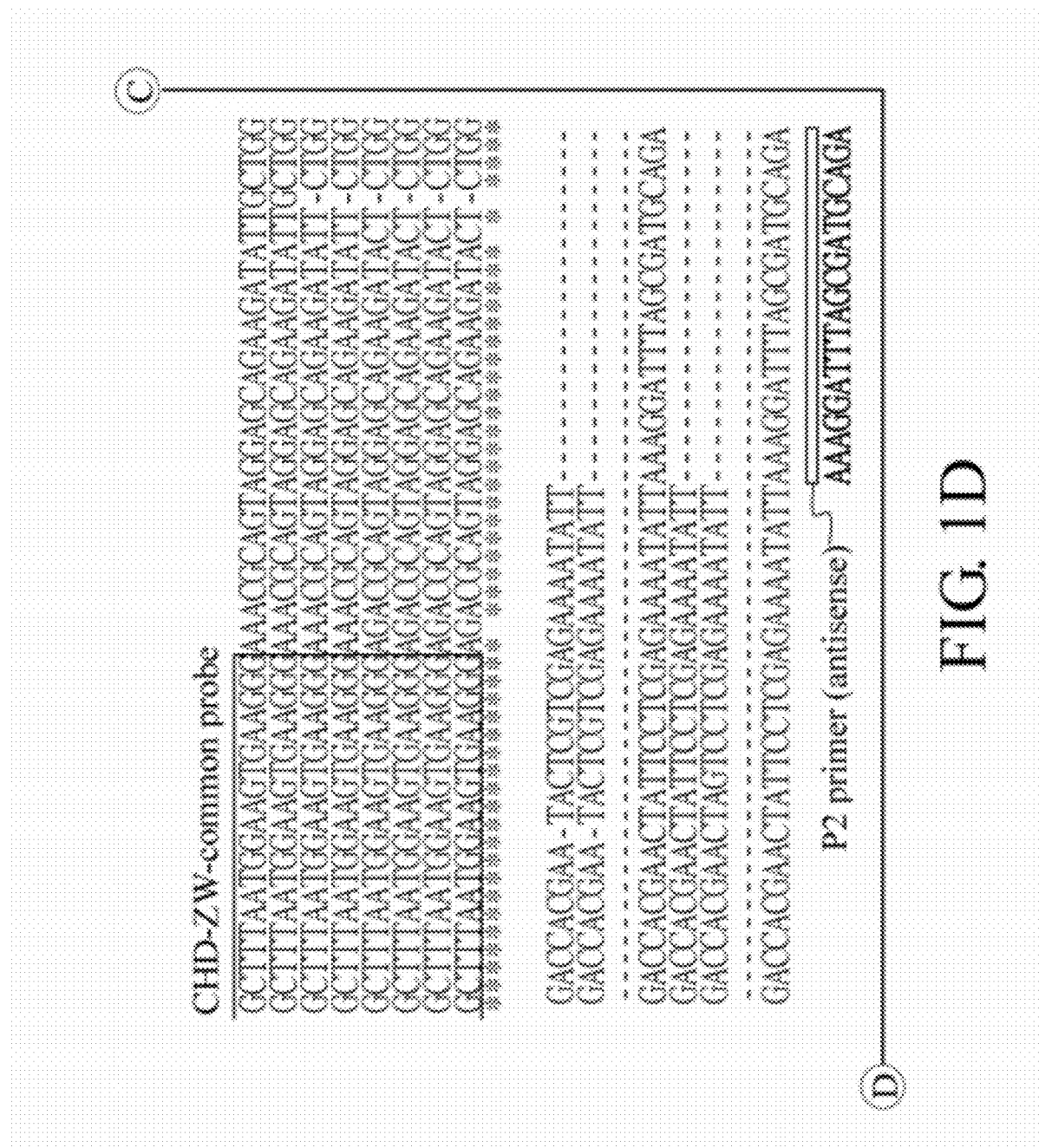
Figure 2A:
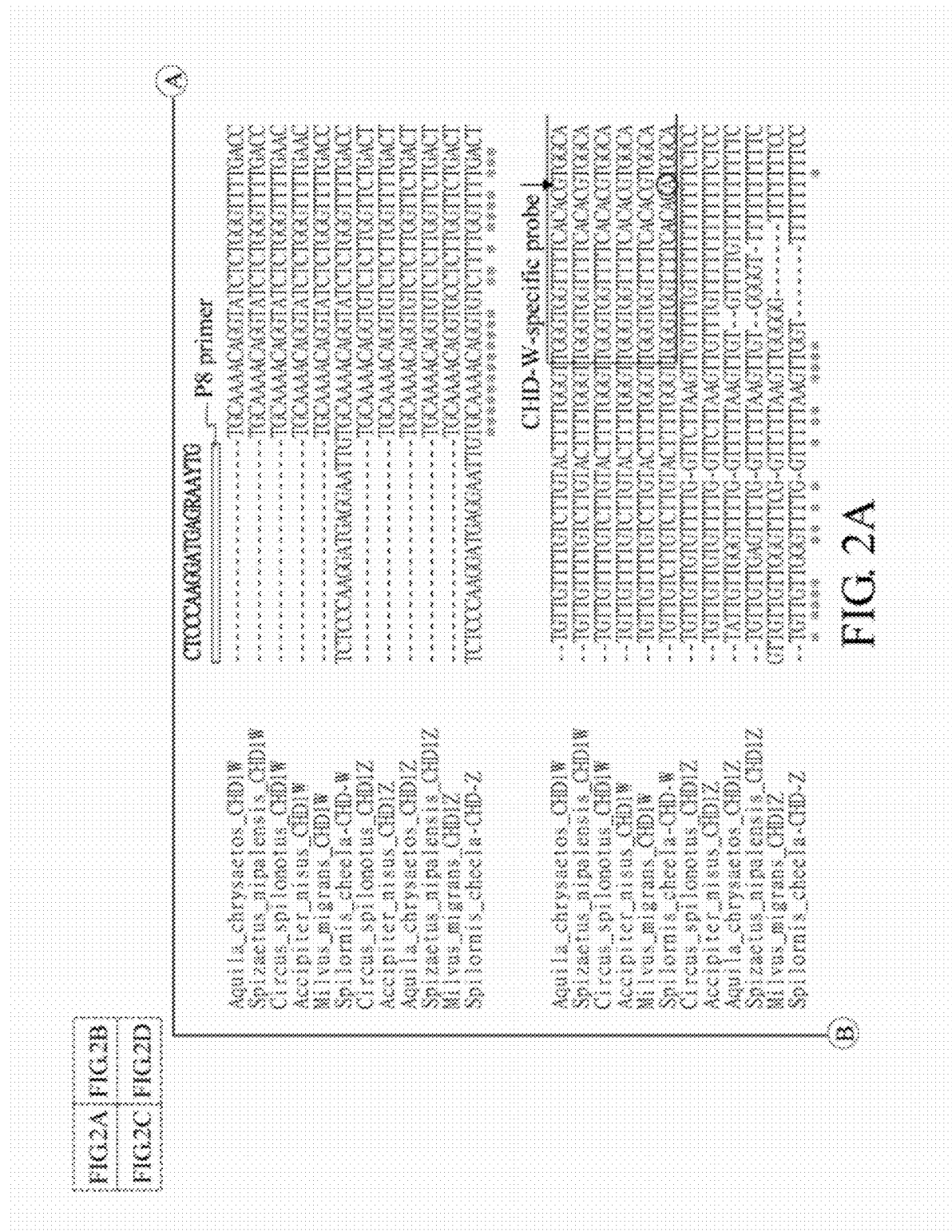
Figure 2D:
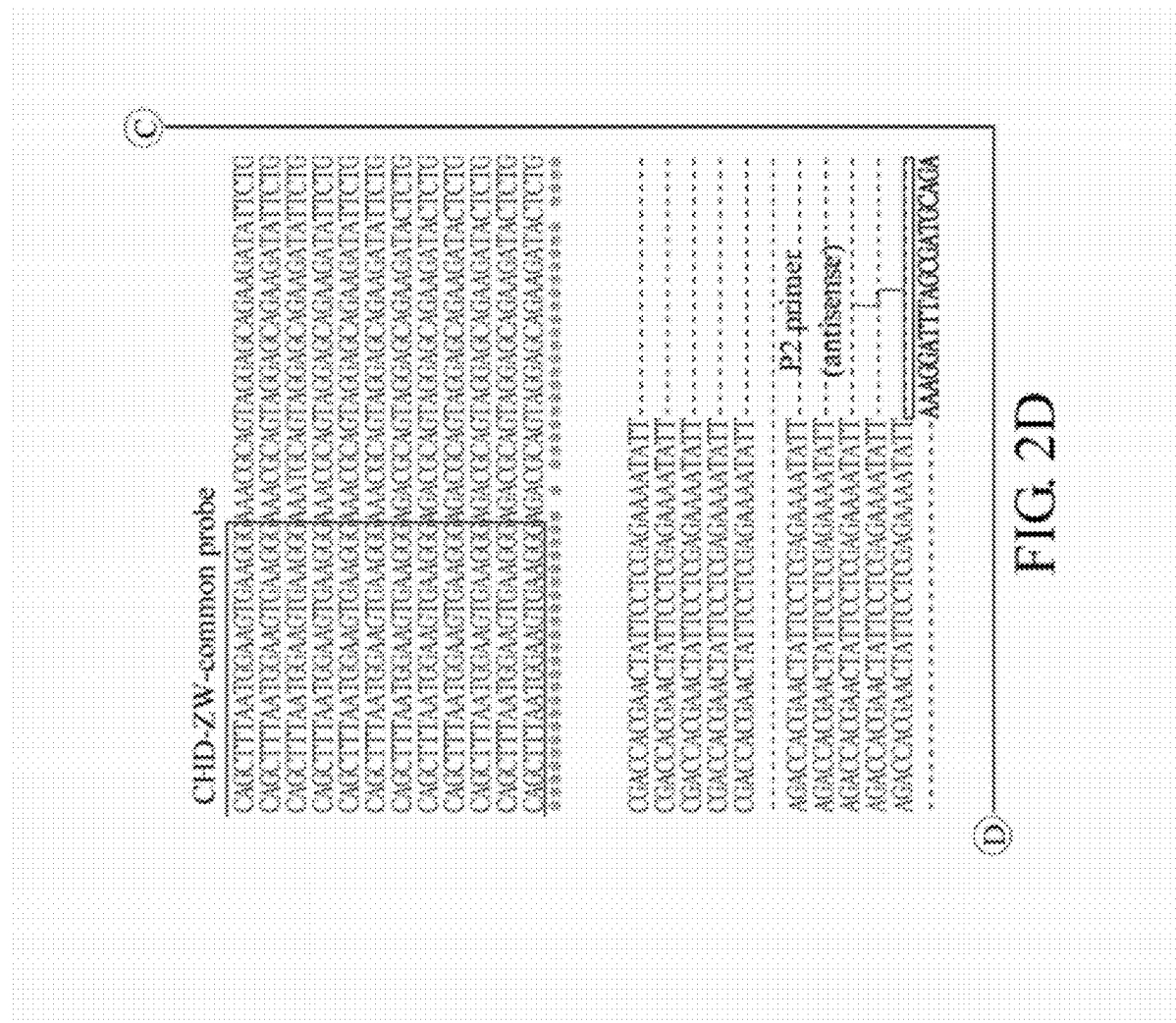
Figure 3:
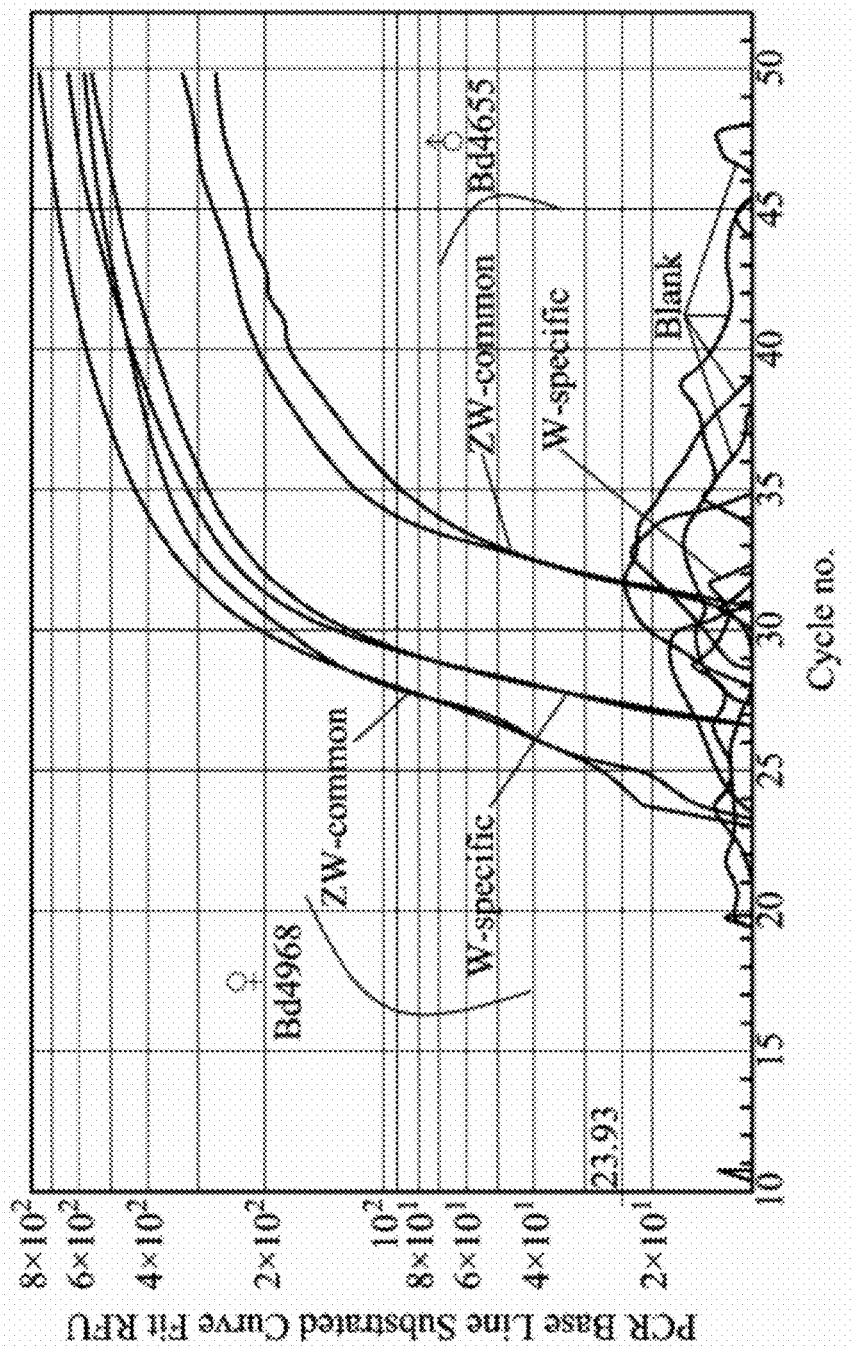
Figure 4:
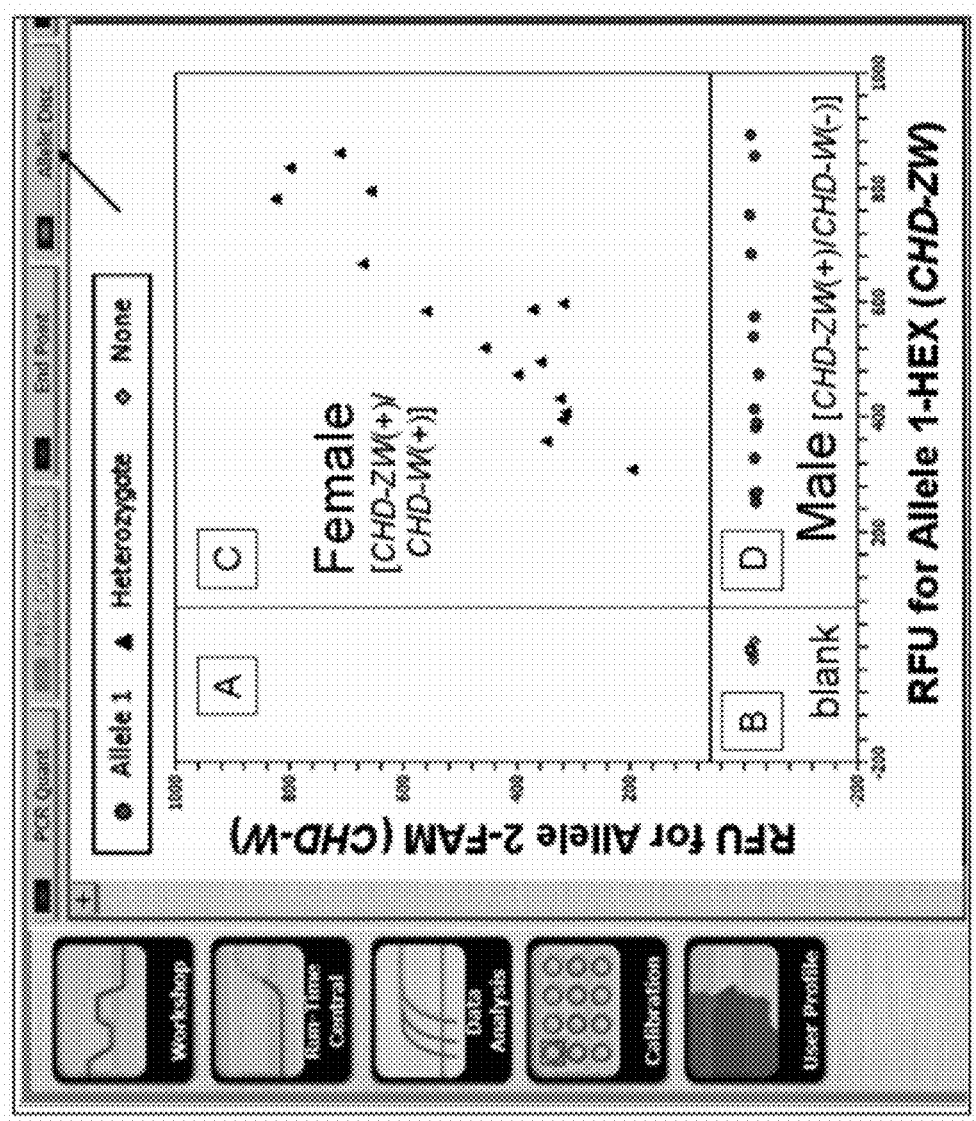

FIG. 3 shows a real-time PCR curve for gender identification of *Spilornis cheela hoya* (*S. c. hoya*); and FIG. 4 shows a demonstration of high-throughput gender identification of *Spilornis cheela hoya* (*S. c. hoya*) by probes with the sequences of the invention and auto-gender calling by software.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a method for gender identification of eagles with probe-based real-time PCR. The detailed descriptions and processes are shown in the following.

Probe designing

The eagle species with similar CHD-Z and CHD-W gene sequences are selected. In one embodiment, the eagles may belong to a family of Accipitridae or further belongs to a subfamily of Accipitrinae. For example, the eagle may comprise *Aquila chrysaetos, Spizaetus nipalensis, Circus spilonotus, Accipiter nisus, Milvus migrans* or *Spilornis cheela hoya*.

The CHD-Z and CHD-W sequences of the species selected above are determined by sequencing their P2 SEQ ID NO:5)/P8(SEQ ID NO:6) amplicons, respectively (Mol Cell Probes 2004;18:193-6, Curr Sci 2007;92:659-62, and Zoolog Sci 2003;20:339-44). The sequences of P2/P8 amplicons of CHD-Z and CHD-W of the eagle selected above are based upon sequence alignment. Then SEQ ID. No. 1 or the complementary sequence thereof for the CHD-Z and CHD-W common region, and SEQ ID. No. 2 or the complementary sequence thereof for the CHD-W specific region of the eagle selected above are respectively recognized.

SEQ ID. No. 1 is 38 nucleotides in length and SEQ ID. No. 2 is 44 nucleotides in length. A sequence of a first probe for the CHD-ZW common region may be designed in the range of SEQ ID. No. 1 or the complementary sequence thereof, and a sequence of a second probe for the CHD-W specific region may be designed in the range of SEQ ID. No. 2 or the complementary sequence thereof.

In one embodiment, the sequence of the first probe is a sequence with about 15-38 nucleotides in length of SEQ ID No. 1 or the complementary sequence thereof and the sequence of the second probe is a sequence with about 15-44 nucleotides in length of SEQ ID No. 2 or the complementary sequence thereof. In other embodiments, the sequence of the first probe is SEQ ID. No. 3 or the complementary sequence thereof, and the sequence of the second probe is SEQ ID. No. 4 or the complementary sequence thereof. Preferably, the sequence of the first probe may be SEQ ID. No. 3 and the sequence of the second probe may be SEQ ID. No. 4. It is noted that SEQ ID. No. 3 and SEQ ID. No. 4 are a part of SEQ ID. No. 1 and SEQ ID. No. 2, respectively.

The first probe and the second probe may be artificial. Furthermore, the 5' ends of the first probe and the second probe may be labeled with a first fluorescent dye and a second fluorescent dye, respectively, and the first fluorescent dye may be different from the second fluorescent dye. The 3' ends of the first probe and the second probe are both labeled with quencher dyes. The first fluorescent dye may comprise 6-carboxyfluorescein (FAM), fluorescein isothiocyanate (FITC), 2,7-dimethoxy-4,5-dichloro-6-carboxyfluorescein (JOE) or hexachloro-6-carboxyfluorescein (HEX) and the second fluorescent dye may comprise 6-carboxyfluorescein (FAM), fluorescein isothiocyanate (FITC), 2,7-dimethoxy-4,5-dichloro-6-carboxyfluorescein (JOE) or hexachloro-6-carboxyfluorescein (HEX). However, FAM and FITC are not recommended to use at the same time due to the similar emission of color (521 and 519 nm, respectively). The quencher dye may comprise 6-carboxytetramethyl-rhodamine (TAMRA) or dimethylaminoazosulphonic acid (Dabsyl).

DNA Sample of the Eagle

A DNA sample of an eagle used to identify gender is provided. The DNA sample may be extracted from a blood sample or a tissue sample of the eagle.

Probe-based Real Time PCR

A probe-based real time PCR is performed to identify gender of the eagle. The DNA sample mentioned above is used as a template and a universal primer pair P2 (SEQ ID NO:5) and P8 (SEQ ID NO:6) is used as a primer. Moreover, the first probe and the second probe mentioned previously are used as probes. In one embodiment, the sequence first probe is SEQ ID. No. 3 and the 5' end of the first probe is labeled with hexachloro-6-carboxyfluorescein (HEX) and the 3' end of the first probe is labeled with 6-carboxytetramethyl-rhodamine (TAMRA). In another embodiment, the sequence first probe is SEQ ID. No. 4 and the 5' end of the second probe is labeled with 6-carboxyfluorescein (FAM) and the 3' end of the second probe is labeled with 6-carboxytetramethyl-rhodamine (TAMRA). In one embodiment, the eagle may comprise *Aquila chrysaetos , Spizaetus nipalensis , Circus spilonotus, Accipiter nisus, Milvus migrans* or *Spilornis cheela hoya* and *Spilornis cheela hoya* preferably.

After the probe-based real time PCR has been completed, a result of the probe-based real-time PCR is analyzed. If the result is positive for both the first and the second fluorescent dye, the eagle is a female, and if the result is positive for only the first fluorescent dye, the eagle is a male.

EXAMPLE

Identifying Eagles With Similar CHD Sequences and Designing Common Probes for Gender Identification The CHD-Z and CHD-W gene sequences of *Spilornis cheela hoya* (*S. c. hoya*) (DQ885238 (SEQ ID. NO:8), and DQ885237 (SEQ ID. NO:9), respectively) were used to identify other species of eagles with similar sequences by BLAST analysis (Nucleic Acids Res 2004;32:W20-5). The CHD-Z and CHD-W gene sequences of the similar species were compared and aligned using the Biology Workbench 3.2. After alignment inspection, many species listed in the panel of BLAST hits were excluded, because their sequences were too diverse (low score and high E-value in BLAST analysis) to design common probes for gender identification of various species of eagles.

Length Difference Between CHD-Z and CHD-W Genes of the Same Species

The CHD-Z and CHD-W sequences of the species selected above (listed in FIGS. 1A-1D and FIGS. 2A-2D) were determined by sequencing their P2/P8 amplicons (Mol Cell Probes 2004;18:193-6, Curr Sci 2007;92:659-62 and Zoolog Sci 2003;20:339-44). The length difference between the CHD-Z and CHD-W genes amplified by the P2/P8 primers for each species was calculated by subtracting the deleted regions (indicated by the dashed lines between P8 and P2 primer sequences in FIGS. 1A-1D and FIGS. 2A-2D) for the CHD-Z and CHD-W genes in their aligned sequences of the same species. The same criteria were used to calculate the length difference between the CHD-Z and CHD-W genes in other species.

FIGS. 1A-1D shows sequence alignment of the CHD-Z and CHD-W genes amplified by P2/P8 primers in four species of eagles. The sequences start with the P8 primer and end with the P2 primer. The CHD-W-specific and CHD-ZW-common probes are indicated by boxes. The star symbols indicate the conserved region between the CHD-Z and CHD-W genes of all sequences in the tested species. The primer sequences were sometimes not included. The sequence of the *S. c. hoya* was incomplete and shorter than the others, especially at the end of the P2 primer. All accession numbers of CHD-Z-CHD-W genes are described in the following, such as *Circaetus gallicus* (*C. gallicus*) AY313610 (SEQ ID. NO:10)/AY313609 (SEQ ID. NO:11), Gyps indicus (*G. indicus*) DQ156155 (SEQ ID. NO:12)/DQ156156 (SEQ ID. NO:13), *Gyps bengalensis* (*G. bengalensis*) DQ156153 (SEQ ID. NO:14)/DQ156154 (SEQ ID. NO:15), and *Spilornis cheela hoya* (*S. c. hoya*) DQ885238 (SEQ ID. NO:8)/DQ885237 SEQ ID. NO:9), respectively. Solid squares after the name of the species indicate the tested species, *S. c. hoya*.

FIGS. 2A-2D shows sequence alignment of the CHD-Z and CHD-W genes amplified by the P2/P8 primers in the five species of eagles (*A. chrysaetos, S. nipalensis, C. spilonotus, A. nisus,* and *M. migrans*) compared with the *S. c. hoya*. All symbols are the same as those described in FIGS. 1A-1D. The major difference between the eagles and the *S. c. hoya* was only one nucleotide, marked with an arrow beside the text of "CHD-W-specific probe", i.e., G vs. A (A is circled in *S. c. hoya*). The probe sequences shown in FIGS. 2A-2D are the complementary strand of the sequence described previously. All accession numbers of CHD-W/CHD-Z genes are described in the following, such as *Accipiter nisus* (*A. nisus*) AB096151 (SEQ ID. NO:16)/AB096152 (SEQ ID. NO:17), *Spizaetus nipalensis* (*S. nipalensis*) AB096149 (SEQ ID. NO:18)/AB096150 (SEQ ID. NO:19), *Aquila chrysaetos* (*A. chrysaetos*) AB096147 (SEQ ID. NO:20)/AB096148 (SEQ ID. NO:21), *Circus spilonotus* (*C. Spilonotus*) AB096145 (SEQ ID. NO:22)/AB096146 (SEQ ID. NO:23), and *Milvus migrans* (*M. migrans*) AB096141 SEQ ID. NO:24)/ AB096142 (SEQ ID. NO:25), respectively.

(DQ885238 (SEQ ID. NO:8)/DQ885237 (SEQ ID. NO:9)) were found using BLAST analysis. According to the criteria described above, nine species of eagles (FIGS. 1A-1D and FIGS. 2A-2D) with the highest score and lowest E values for the BLAST analysis were chosen (data not shown). Their sequence information was presented as the GenBank accession nos. of CHD-Z/CHD-W, followed by the length difference between P2/P8-amplified PCR products of the two genes: *C. gallicus* AY313610 (SEQ ID. NO:10)/AY313609 (SEQ ID. NO:11) (9-bp), *G. indicus* DQ156155 (SEQ ID. NO:12)/DQ156156 (SEQ ID. NO:13) (6-bp), *G. bengalensis* DQ156153 (SEQ ID. NO:14)/DQ156154 SEQ ID. NO:15) (5-bp), *A. nisus* AB096152 (SEQ ID. NO:17)/ AB096151 (SEQ ID. NO:16) (4-bp), *Spizaetus nipalensis* AB096150 (SEQ ID. NO:19)/AB096149 (SEQ ID. NO:18) (8-bp), *A. chrysaetos* (SEQ ID. NO:21) (SEQ ID. NO:20)4409-64-4-g (3-bp), *Circus spilonotus* (SEQ ID. NO:23)/AB096145 (SEQ ID. NO:22)(4-bp), *Milvus migrans* AB096142 (SEQ ID. NO:25)/AB096141 (SEQ ID. NO:24) (2-bp), and *S. c. hoya* DQ885238 (SEQ ID. NO:8)/DQ885237 (SEQ ID. NO:9) (13-bp). All of the eagles belong to the same order of Falconiformes, family of Accipitridae, and subfamily of Accipitrinae, but to different genera. Therefore, the length difference between the CHD-Z and CHD-W PCR products using the P2/P8 primers ranged from 2-bp to 13-bp for the species (too small to be resolved by a conventional agarose gel).

Given the sequence similarity of the CHD-Z and CHD-W genes in the species of eagles, novel universal probes for gender identification of the birds were able to be designed. The results of the sequence alignment of the CHD-Z and CHD-W genes from the four species (*C. gallicus, G. indicus, G. bengalensis* vs. *S. c. hoya*) and the six species (*A. nisus, S. nipalensis, A. chrysaetos, C. spilonotus, M migrans* vs. *S. c. hoya*) of eagles are shown FIGS. 1A-1D and FIGS. 2A-2D, respectively). The ends of the alignments were all flanked by the P8 and P2 primers (Mol Ecol 1998;7:1071-5). Both the CHD-W-specific and CHD-ZW-common probes were marked with boxes around them (FIGS. 1A-1D and FIGS. 2A-2D, respectively). The sequences for the probes are the sequences of the complementary strands shown in FIGS. 1A-1D and FIGS. 2A-2D. It is to be noted that *C. gallicus, G. indicus, G. bengalensis* and *S. c. hoya* shared the same sequence in the CHD-W-specific region (FIGS. 1A-1D), whereas *A. nisus, S. nipalensis, A. chrysaetos, C. spilonotus,* and *M migrans* had only one nucleotide difference (G) in the CHD-W- specific region, as compared to the nucleotide A in the *S. c. hoya* as well as in the species described in FIGS. 1A-1D (i.e., SEQ ID NO:7, in which the nucleotide at position 17 is G instead of A, FIGS. 2A-2D). In contrast, the CHD-ZW-common region was completely conserved in the nine species of eagles (FIGS. 1A-1D and FIGS. 2A-2D). Consequently, it is determined that the CHD-W-specific and CHD-ZW-common probes combined with the P2/P8 primers were suitable for subsequent tests of real-time PCR-based gender identification.

Samples Collection and DNA Extraction

Thirteen blood samples (Birds 12-24) and two tissue samples (Birds 4966 and 4968) from the *S. c. hoya* were collected, with the official permission of the Kenting National Park, Taiwan, and Taiwan Endemic Species Research Institute, respectively. Based on anatomical inspection, Bird 4966 and Bird 4968, was identified as male and female, respectively. Blood and tissue DNA was extracted by the QIAamp DNA Blood Mini Kit and DNeasy tissue kit (Qiagen, Valencia, Calif., USA).

Molecular Gender Identification Using Probes of the Invention and P2/P8 Primers

The sequences of probes for the CHD-ZW common and CHD-W-specific regions of the *S. c. hoya* were 5'-HEX-(SEQ ID NO:3)-TAMRA and, 5'-FAM-(SEQ ID NO:4)-TAMRA, respectively and the sequences were complementary to those shown in FIGS. 1 and 2. The universal primer pair P2 SEQ ID NO:5) and P8 SEQ ID NO:6) were reported previously (Mol Ecol 1998;7:1071-5). The locations of the primers and probes are shown (FIGS. 1 and 2). To perform the probe-based real-time PCR, DNA samples were added to the PCR reaction mixture (10 µL), which contained 1xPCR buffer, 6 mM $MgCl_2$, 0.2 mM dNTPs, 2.5 U Taq enzyme (Invitrogen Inc., Sao Paulo, SP, Brazil), 0.16 µM primers (Gen-Script Corp., Piscataway, NJ, USA), 200 mM probes for the CHD-ZW common or CHD- W-specific regions of the *S. c. hoya* (Sigma-Proligo Inc., The Woodlands, TX, USA) (sequences as mentioned above), and 10-20 ng DNA. The PCR was performed by the two-step program built into the iQ5 real-time system (Bio-Rad Laboratories, Hercules, Calif., USA), as follows: 95° C. for 10 min, 92° C. for 15 s, and 60° C. for 1 min (total of 50 cycles).

The *S. c. hoya*, DNA from one male and one female (confirmed by anatomical inspection) were used to delineate the real-time PCR curve by the probes mentioned previously (FIG. 3). FIG. 3 shows a real-time PCR curve for gender identification of eagles. Anatomically confirmed female and male (Bird 4968 and Bird 4655) were used as controls. All tested birds were analyzed in duplicate. W-specific and ZW-common indicated the probes for the CHD-W specific and CHD-ZW-common regions, respectively. And relative fluorescence unit (RFU) indicated relative fluorescence unit. Samples of Bird 4968 and Bird 4655 had a positive fluorescence signal of HEX (indicated by ZW common). Therefore, they were used as the positive control for both the CHD-Z and CHD-W genes, representing the CHD-ZW-common sequence existing in both female and male birds. Conversely, samples of Bird 4968 and Bird 4655 had the presence or absence of FAM fluorescence (indicated by W-specific). Therefore, they served as the positive and negative controls for the CHD-W gene, representing female and male birds, respectively. Moreover, the blank control had very low fluorescence intensities for both FAM and HEX, suggesting that probes of the invention did not detect false positives. Similarly, samples of Birds 12, 14, 15, 17, 19, 20, and 23 were identified as females, whereas other samples listed in this study were ascertained to be males in the real-time PCR curve (data not shown).

In addition to the real-time PCR curve assay (FIG. 3), the data in two dimensions using the axis of allele 1 (HEX-CHD-ZW) and allele 2 (FAM-CHD-W), is shown in FIG. 4. FIG. 4 shows a demonstration of high-throughput gender identification of eagles by mentioned probes and auto-gender calling by software. FIG. 4 is the screen view of a real-time PCR analysis software (iQ5, Bio-rad) after performing the function of "allele discrimination" as indicated by the arrow. All tested birds (n=15) were analyzed in duplicate. Part (A) of FIG. 4 shows the region for internal negative control for the CHD probes. Part (B) of FIG. 4 shows the blank sample for the template-negative control, representing the fluorescence background of the probes (Part (C) and (D)). The CHD-ZW probe was common to both male and female. The CHD-W probe was only specific for females. The anatomically confirmed female (Bird 4968) and male (Bird 4655) controls were included in the test and their fluorescence intensities are shown in Table 1. Allele 1 and heterozygote were regarded as the male and female (as illustrated in Part (A)-(D) of FIG. 4), respectively. Complete data is provided in Table 1. Because birds are always CHD-Z-positive, it is unreasonable to expect to find birds with only the CHD-W gene. Therefore, both regions in FIG. 4 (on the left, Part (A) and (B)) were chosen as the negative controls for the presence and absence of DNA templates, respectively. Samples with the heterozygous alleles representing both CHD-W-positive and CHD-ZW-positive, were predicted to be females (i.e., Birds 12, 14, 15, 17, 19, 20, 23, and 4968). Conversely, samples with allele 1 (CHD-ZW-common probe) alone representing both the CHD-ZW-positive and CHD-W-negative were predicted to be males (i.e., Birds 13, 16, 18, 21, 22, 24, and 4966). Finally, all gender information of the tested samples was immediately displayed in a chart and auto-called in a high-throughput manner (not shown, detailed in Table 1). Moreover, the chart's data set was exported to Microsoft Excel software for statistical analysis (Table 1).

TABLE 1

Summary of gender identification of the S. c. hoya (n = 15) using probes of the example

| Well | ID #[a] | RFU1[b] (CHD-ZW) | RFU2[b] (CHD-W) | Call[c] |
|---|---|---|---|---|
| A02 | Bird 12 | 586.77 | 372.07 | Heterozygote |
| A03 | Bird 12 | 495.69 | 358.56 | Heterozygote |
| A04 | Bird 20 | 833.72 | 799.85 | Heterozygote |
| A05 | Bird 20 | 859.60 | 713.03 | Heterozygote |
| B02 | Bird 13 | 266.27 | −18.06 | Allele 1 |
| B03 | Bird 13 | 251.43 | −20.23 | Allele 1 |
| B04 | Bird 21 | 854.44 | −17.86 | Allele 1 |
| B05 | Bird 21 | 891.52 | −10.82 | Allele 1 |
| C02 | Bird 14 | 407.40 | 314.45 | Heterozygote |
| C03 | Bird 14 | 431.69 | 324.50 | Heterozygote |
| C04 | Bird 22 | 575.08 | −17.62 | Allele 1 |
| C05 | Bird 22 | 540.09 | −15.82 | Allele 1 |
| D02 | Bird 15 | 307.87 | 197.74 | Heterozygote |
| D03 | Bird 15 | 394.99 | 319.84 | Heterozygote |
| D04 | Bird 23 | 779.47 | 825.01 | Heterozygote |
| D05 | Bird 23 | 666.31 | 672.20 | Heterozygote |
| E02 | Bird 16 | 473.88 | −25.19 | Allele 1 |
| E03 | Bird 16 | 413.67 | −17.78 | Allele 1 |
| E04 | Bird 24 | 751.58 | −9.39 | Allele 1 |
| E05 | Bird 224 | 683.89 | −11.95 | Allele 1 |
| E08 | Blank | −2.86 | −9.52 | None |
| E09 | Blank | −5.54 | −13.25 | None |
| F02 | Bird 17 | 357.35 | 348.55 | Heterozygote |
| F03 | Bird 17 | 520.33 | 456.77 | Heterozygote |
| G02 | Bird 18 | 381.13 | −19.83 | Allele 1 |
| G03 | Bird 18 | 390.18 | −22.04 | Allele 1 |
| G04 | Bird 4966[d] | 268.83 | −22.10 | Allele 1 |
| G05 | Bird 4966[d] | 327.92 | −17.89 | Allele 1 |
| G08 | Blank | 10.16 | −18.07 | None |
| G09 | Blank | −23.48 | −16.48 | None |
| H02 | Bird 19 | 597.51 | 319.02 | Heterozygote |
| H03 | Bird 19 | 473.46 | 398.29 | Heterozygote |
| H04 | Bird 4966[d] | 793.04 | 657.46 | Heterozygote |
| H05 | Bird 4966[d] | 584.12 | 560.44 | Heterozygote |
| H08 | Blank | −11.18 | −15.88 | None |
| H09 | Blank | −5.45 | −10.83 | None |

[a]All samples were tested in duplicates, e.g., wells A02 and A03 indicate the same sample ID# Bird 12.
[b]Relative fluorescence unit. RFU1, RFU of allele 1 (CHD-ZW-common probe); RFU2, RFU of allele 2 (CHD-W-specific probe).
[c]Heterozygote indicated female, i.e., RFU1 (+) and RFU2 (+). None indicated no calling for gender.
[d]The female and male controls were confirmed by anatomical inspection.

In Table 1, all heterozygotes had positive signals of both RFU1 and RFU2, i.e., fluorescence for the CHD-ZW and CHD-W probes, respectively. For male birds, all RFU1 signals were positive, whereas all RFU2 were negative. For the blank control, almost all RFU1 and RFU2 signals were negative, except for the well G08. Although the well G08 had a positive RFU1 signal (10.16), the value was very small compared to the values (range, 891.52-251.50 in all female and male samples). Furthermore, no signal was detected in the region of Part (A) of FIG. 4. Therefore, the probes allowed accurate and efficient gender identification of the S. c. hoya in a high-throughput manner.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for gender identification of eagles with probe-based real-time PCR, comprising:
   (a) providing a DNA of an eagle;
   (b) performing a probe-based real-time PCR using the DNA as a template, a universal primer pair P2 and P8 as a primer pair and a first probe and a second probe as probes, wherein the 5' ends of the first probe and the second probe are labeled with a first fluorescent dye and the second fluorescent dye, respectively, the 3' ends of the first probe and the second probe are both labeled with quencher dyes and the first fluorescent dye is different from the second fluorescent dye, and wherein a sequence of the first probe is a sequence with about 15-38 nucleotides in length of SEQ ID No. 1 or the complementary sequence thereof and a sequence of the second probe is a sequence with about 15-44 nucleotides in length of SEQ ID No. 2 or the complementary sequence thereof; and
   (c) analyzing a result of the probe-based real-time PCR, wherein if the result is positive for both the first and the second fluorescent dye, the eagle is a female, and if the result is positive for only the first fluorescent dye, the eagle is a male.

2. The method as claimed in claim 1, wherein the eagle belongs to a family of Accipitridae.

3. The method as claimed in claim 1, wherein the eagle belongs to a subfamily of Accipitrinae.

4. The method as claimed in claim 1, wherein the eagle comprises *Aquila chrysaetos, Spizaetus nipalensis, Circus spilonotus, Accipiter nisus, Milvus migrans* or *Spilornis cheela hoya*.

5. The method as claimed in claim 1, wherein the first fluorescent dye comprises 6-carboxyfluorescein (FAM), fluorescein isothiocyanate (FITC), 2,7-dimethoxy-4,5-dichloro-6-carboxyfluorescein (JOE) or hexachloro-6-carboxyfluorescein (HEX).

6. The method as claimed in claim 1, wherein the second fluorescent dye comprises 6-carboxyfluorescein (FAM), fluorescein isothiocyanate (FITC), 2,7-dimethoxy-4,5-dichloro-6-carboxyfluorescein (JOE) or hexachloro-6-carboxyfluorescein (HEX).

7. The method as claimed in claim 1, wherein the quencher dye comprises 6-carboxytetramethyl-rhodamine (TAMRA) or dimethylaminoazosulphonic acid (Dabsyl).

8. The method as claimed in claim 1, wherein the sequence of the first probe is a sequence with 28 nucleotides in length of SEQ ID No. 1 or the complementary sequence thereof.

9. The method as claimed in claim 1, wherein the sequence of the first probe is a sequence with 24 nucleotides in length of SEQ ID No. 2 or the complementary sequence thereof.

10. The method as claimed in claim 1, wherein the sequence of the first probe is SEQ ID. No. 3 or the complementary sequence thereof.

11. The method as claimed in claim 1, wherein the sequence of the second probe is SEQ ID. No. 4 or the complementary sequence thereof.

12. The method as claimed in claim 1, wherein the sequence of the first probe is SEQ ID. No. 3 and the sequence of the second probe is SEQ No. 4.

* * * * *